(12) United States Patent
Duecker et al.

(10) Patent No.: US 6,183,990 B1
(45) Date of Patent: Feb. 6, 2001

(54) COMPOUNDS

(75) Inventors: Klaus Norbert Duecker, Bishop's Stortford (GB); Thierry Paul Gerard Calmels, Pace (FR)

(73) Assignee: SmithKline Beecham, plc (GB)

( * ) Notice: Under 35 U.S.C. 154(b), the term of this patent shall be extended for 0 days.

(21) Appl. No.: 09/311,924

(22) Filed: May 14, 1999

(30) Foreign Application Priority Data

May 14, 1998 (GB) .................................................. 9801409

(51) Int. Cl.[7] .............................. C12P 21/06; C12N 15/85
(52) U.S. Cl. ...................... 435/69.1; 536/23.1; 536/23.5; 435/320.1; 435/7.1; 435/325; 436/501; 530/350; 530/300; 530/825; 424/243.1
(58) Field of Search .................................. 536/23.1, 23.5; 435/320.1, 69.1, 6, 7.1, 325; 436/501; 530/350, 300, 825; 424/243.1

(56) References Cited

U.S. PATENT DOCUMENTS 5,691,147 * 11/1997 Draetta et al. ........................ 435/7.1

FOREIGN PATENT DOCUMENTS

WO 95/33819   2/1995  (WO) .

OTHER PUBLICATIONS

Waterston RH. Direct Submission, Jun. 12, 1998, Accession #AC 005041, Genome Sequencing Center.*
GenBank Accession No. U54638, Reid et al., Jul. 14, 1996.
GenBank Accession No. W72722, Hillier et al., Oct. 16, 1996.
GenBank Accession No. AA928859, National Cancer Institute, Cancer Genome Anatomy Project, Jul. 7, 1998.
Reid et al. "Rhotekin, a New Putative Target for Rho Bearing Homology to a Serine/Threonine Kinase, PKN, and Rhonophilin in the Rho–binding Domain", vol. 271(23), pp. 13556–13560 (1996).

* cited by examiner

Primary Examiner—Christopher S. F. Low
Assistant Examiner—Hope A. Robinson
(74) Attorney, Agent, or Firm—William T. Han; Ratner & Prestia; William T. King

(57) ABSTRACT

Rhotekin polypeptides and polynucleotides and methods for producing such polypeptides by recombinant techniques are disclosed. Also disclosed are methods for utilizing rhotekin polypeptides and polynucleotides in diagnostic assays.

8 Claims, No Drawings

COMPOUNDS

FIELD OF THE INVENTION

This invention relates to newly identified polypeptides and polynucleotides encoding such polypeptides, to their use in diagnosis and in identifying compounds that may be agonists, antagonists that are potentially useful in therapy, and to production of such polypeptides and polynucleotides.

BACKGROUND OF THE INVENTION

The drug discovery process is currently undergoing a fundamental revolution as it embraces "functional genomics", that is, high throughput genome- or gene-based biology. This approach as a means to identify genes and gene products as therapeutic targets is rapidly superseding earlier approaches based on "positional cloning". A phenotype, that is a biological function or genetic disease, would be identified and this would then be tacked back to the responsible gene, based on its genetic map position.

Functional genomics relies heavily on high-throughput DNA sequencing technologies and the various tools of bioinformatics to identify gene sequences of potential interest from the many molecular biology databases now available. There is a continuing need to identify and characterise further genes and their related polypeptides/proteins, as targets for drug discovery.

SUMMARY OF THE INVENTION

The present invention relates to rhotekin, in particular rhotekin polypeptides and rhotekin polynucleotides, recombinant materials and methods for their production. Such polypeptides and polynucleotides are of interest in relation to methods of treatment of certain diseases, including, but not limited to, cancer, cardiovascular disorders, brain disorders, developmental disorders, cytoskeletal-associated disorders and signal transduction related diseases, hereinafter referred to as "diseases of the invention". In a further aspect, the invention relates to methods for identifying agonists and antagonists (e.g., inhibitors) using the materials provided by the invention, and treating conditions associated with rhotekin imbalance with the identified compounds. In a still further aspect, the invention relates to diagnostic assays for detecting diseases associated with inappropriate rhotekin activity or levels.

DESCRIPTION OF THE INVENTION

In a first aspect, the present invention relates to rhotekin polypeptides. Such polypeptides include:

(a) an isolated polypeptide encoded by a polynucleotide comprising the sequence of SEQ ID NO:1;

(b) an isolated polypeptide comprising a polypeptide sequence having at least 95%, 96%, 97%, 98%, or 99% identity to the polypeptide sequence of SEQ ID NO:2;

(c) an isolated polypeptide comprising the polypeptide sequence of SEQ ID NO:2;

(d) an isolated polypeptide having at least 95%, 96%, 97%, 98%, or 99% identity to the polypeptide sequence of SEQ ID NO:2;

(e) the polypeptide sequence of SEQ ID NO:2; and (f) an isolated polypeptide having or comprising a polypeptide sequence that has an Identity Index of 0.96, 0.97, 0.98, or 0.99 compared to the polypeptide sequence of SEQ ID NO:2;

(g) fragments and variants of such polypeptides in (a) to (f).

Polypeptides of the present invention are believed to be members of the Rho effectors family of polypeptides. They are therefore of interest because they bind specifically to GTP-activated Rho proteins and interact with downstream components of Rho-dependent signaling pathways. Interestingly, this gene is located in an area on chromosome 2 which has recently been identified to contain a susceptibility locus for Parkinson's disease (T Gasser et al., Nature Genetics 18: 262–265, 1998).

The biological properties of the rhotekin are hereinafter referred to as "biological activity of rhotekin" or "rhotekin activity." Preferably, a polypeptide of the present invention exhibits at least one biological activity of rhotekin.

Polypeptides of the present invention also includes variants of the aforementioned polypeptides, including all allelic forms and splice variants. Such polypeptides vary from the reference polypeptide by insertions, deletions, and substitutions that may be conservative or non-conservative, or any combination thereof. Particularly preferred variants are those in which several, for instance from 50 to 30, from 30 to 20, from 20 to 10, from 10 to 5, from 5 to 3, from 3 to 2, from 2 to 1 or 1 amino acids are inserted, substituted, or deleted, in any combination.

Preferred fragments of polypeptides of the present invention include an isolated polypeptide comprising an amino acid sequence having at least 30, 50 or 100 contiguous amino acids from the amino acid sequence of SEQ ID NO:2, or an isolated polypeptide comprising an amino acid sequence having at least 30, 50 or 100 contiguous amino acids truncated or deleted from the amino acid sequence of SEQ ID NO:2. Preferred fragments are biologically active fragments that mediate the biological activity of rhotekin, including those with a similar activity or an improved activity, or with a decreased undesirable activity. Also preferred are those fragments that are antigenic or immunogenic in an animal, especially in a human.

Fragments of the polypeptides of the invention may be employed for producing the corresponding full-length polypeptide by peptide synthesis; therefore, these variants may be employed as intermediates for producing the full-length polypeptides of the invention. The polypeptides of the present invention may be in the form of the "mature" protein or may be a part of a larger protein such as a precursor or a fusion protein. It is often advantageous to include an additional amino acid sequence that contains secretory or leader sequences, pro-sequences, sequences that aid in purification, for instance multiple histidine residues, or an additional sequence for stability during recombinant production.

Polypeptides of the present invention can be prepared in any suitable manner, for instance by isolation from naturally occurring sources, from genetically engineered host cells comprising expression systems (vide infra) or by chemical synthesis, using for instance automated peptide synthesizers, or a combination of such methods. Means for preparing such polypeptides are well understood in the art.

In a further aspect, the present invention relates to rhotekin polynucleotides. Such polynucleotides include:

(a) an isolated polynucleotide comprising a polynucleotide sequence having at least 95%, 96%, 97%, 98%, or 99% identity to the polynucleotide sequence of SEQ ID NO:1;

(b) an isolated polynucleotide comprising the polynucleotide of SEQ ID NO:1;

(c) an isolated polynucleotide having at least 95%, 96%, 97%, 98%, or 99% identity to the polynucleotide of SEQ ID NO:1;

(d) the isolated polynucleotide of SEQ ID NO:1;

(e) an isolated polynucleotide comprising a polynucleotide sequence encoding a polypeptide sequence having at least 95%, 96%, 97%, 98%, or 99% identity to the polypeptide sequence of SEQ ID NO:2;

(f) an isolated polynucleotide comprising a polynucleotide sequence encoding the polypeptide of SEQ ID NO:2;

(g) an isolated polynucleotide having a polynucleotide sequence encoding a polypeptide sequence having at least 95%, 96%, 97%, 98%, or 99% identity to the polypeptide sequence of SEQ ID NO:2;

(h) an isolated polynucleotide encoding the polypeptide of SEQ ID NO:2;

(i) an isolated polynucleotide having or comprising a polynucleotide sequence that has an Identity Index of 0.95, 0.96, 0.97, 0.98, or 0.99 compared to the polynucleotide sequence of SEQ ID NO:1;

(j) an isolated polynucleotide having or comprising a polynucleotide sequence encoding a polypeptide sequence that has an Identity Index of 0.95, 0.96, 0.97, 0.98, or 0.99 compared to the polypeptide sequence of SEQ ID NO:2; and polynucleotides that are fragments and variants of the above mentioned polynucleotides or that are complementary to above mentioned polynucleotides, over the entire length thereof.

Preferred fragments of polynucleotides of the present invention include an isolated polynucleotide comprising a nucleotide sequence having at least 15, 30, 50 or 100 contiguous nucleotides from the sequence of SEQ ID NO:1, or an isolated polynucleotide comprising an sequence having at least 30, 50 or 100 contiguous nucleotides truncated or deleted from the sequence of SEQ ID NO:1.

Preferred variants of polynucleotides of the present invention include splice variants, allelic variants, and polymorphisms, including polynucleotides having one or more single nucleotide polymorphisms (SNPs).

Polynucleotides of the present invention also include polynucleotides encoding polypeptide variants that comprise the amino acid sequence of SEQ ID NO:2 and in which several, for instance from 50 to 30, from 30 to 20, from 20 to 10, from 10 to 5, from 5 to 3, from 3 to 2, from 2 to 1 or 1 amino acid residues are substituted, deleted or added, in any combination.

In a further aspect, the present invention provides polynucleotides that are RNA transcripts of the DNA sequences of the present invention. Accordingly, there is provided an RNA polynucleotide that:

(a) comprises an RNA transcript of the DNA sequence encoding the polypeptide of SEQ ID NO:2;

(b) is the RNA transcript of the DNA sequence encoding the polypeptide of SEQ ID NO:2;

(c) comprises an RNA transcript of the DNA sequence of SEQ ID NO:1; or (d) is the RNA transcript of the DNA sequence of SEQ ID NO:1; and RNA polynucleotides that are complementary thereto.

The polynucleotide sequence of SEQ ID NO:1 shows homology with mouse rhotekin (T. Reid et al., J. Biol. Chem., 271: 13556–13560, 1996). The polynucleotide sequence of SEQ ID NO:1 is a CDNA sequence that encodes the polypeptide of SEQ ID NO:2. The polynucleotide sequence encoding the polypeptide of SEQ ID NO:2 may be identical to the polypeptide encoding sequence of SEQ ID NO:1 or it may be a sequence other than SEQ ID NO:1, which, as a result of the redundancy (degeneracy) of the genetic code, also encodes the polypeptide of SEQ ID NO:2.

The polypeptide of the SEQ ID NO:2 is related to other proteins of the Rho effectors family, having homology and/or structural similarity with mouse rhotekin (T. Reid et al., J. Biol. Chem., 271: 13556–13560, 1996).

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one rhotekin activity.

The present invention also relates to partial or other polynucleotide and polypeptide sequences which were first identified prior to the determination of the corresponding full length sequences of SEQ ID NO:1 and SEQ ID NO:2.

Accordingly, in a further aspect, the present invention provides for an isolated polynucleotide which:

(a) comprises a nucleotide sequence which has at least 95% identity, preferably at least 97–99% identity to SEQ ID NO:3 over the entire length of SEQ ID NO:3;

(b) has a nucleotide sequence which has at least 95% identity, preferably at least 97–99% identity, to SEQ ID NO:3 over the entire length of SEQ ID NO:3;

(c) the polynucleotide of SEQ ID NO:3; or (d) a nucleotide sequence encoding a polypeptide which has at least 95% identity, even more preferably at least 97–99% identity, to the amino acid sequence of SEQ ID NO:4, over the entire length of SEQ ID NO:4; as well as the polynucleotide of SEQ ID NO:3.

The present invention further provides for a polypeptide which:

(a) comprises an amino acid sequence which has at least 95% identity, preferably at least 97–99% identity, to that of SEQ ID NO:4 over the entire length of SEQ ID NO:4;

(b) has an amino acid sequence which is at least 95% identity, preferably at least 97–99% identity, to the amino acid sequence of SEQ ID NO:4 over the entire length of SEQ ID NO:4;

(c) comprises the amino acid of SEQ ID NO:4; and (d) is the polypeptide of SEQ ID NO:4;
as well as polypeptides encoded by a polynucleotide comprising the sequence contained in SEQ ID NO:3.

The nucleotide sequence of SEQ ID NO:3 and the peptide sequence encoded thereby are derived from EST (Expressed Sequence Tag) sequences. It is recognized by those skilled in the art that there will inevitably be some nucleotide sequence reading errors in EST sequences (see Adams, M. D. et al, Nature 377 (supp) 3, 1995). Accordingly, the nucleotide sequence of SEQ ID NO:3 and the peptide sequence encoded therefrom are therefore subject to the same inherent limitations in sequence accuracy. Furthermore, the peptide sequence encoded by SEQ ID NO:3 comprises a region of identity or close homology and/or close structural similarity (for example a conservative amino acid difference) with the closest homologous or structurally similar protein.

Polynucleotides of the present invention may be obtained using standard cloning and screening techniques from a cDNA library derived from mRNA in cells of human brain, breast colon, heart, kidney, lung, pancreas, parathyroid, prostate, smooth muscle and whole embryo, (see for instance, Sambrook et al., Molecular Cloning: A Laboratory Manual, 2nd Ed., Cold Spring Harbor Laboratory Press, Cold Spring Harbor, N.Y. (1989)). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself or the coding sequence for the mature polypeptide in reading frame with other coding sequences, such as those encoding a leader or secretory sequence, a pre-, or pro- or prepro- protein sequence, or other fusion peptide portions. For example, a marker sequence that facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Polynucleotides that are identical, or have sufficient identity to a polynucleotide sequence of SEQ ID NO:1, may be used as hybridization probes for cDNA and genomic DNA or as primers for a nucleic acid amplification reaction (for instance, PCR). Such probes and primers may be used to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO:1, typically at least 95% identity. Preferred probes and primers will generally comprise at least 15 nucleotides, preferably, at least 30 nucleotides and may have at least 50, if not at least 100 nucleotides. Particularly preferred probes will have between 30 and 50 nucleotides. Particularly preferred primers will have between 20 and 25 nucleotides.

A polynucleotide encoding a polypeptide of the present invention, including homologs from species other than human, may be obtained by a process comprising the steps of screening a library under stringent hybridization conditions with a labeled probe having the sequence of SEQ ID NO:1 or a fragment thereof, preferably of at least 15 nucleotides; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5=SSC (150 mM NaCl, 15 mM trisodium citrate), 50 mM sodium phosphate (pH7.6), 5=Denhardt's solution, 10% dextran sulfite, and 20 microgram/ml denatured, sheared salmon sperm DNA; followed by washing the filters in 0.1=SSC at about 65° C. Thus the present invention also includes isolated polynucleotides, preferably with a nucleotide sequence of at least 100, obtained by screening a library under stringent hybridization conditions with a labeled probe having the sequence of SEQ ID NO:1 or a fragment thereof preferably of at least 15 nucleotides.

The skilled artisan will appreciate that, in many cases, an isolated cDNA sequence will be incomplete, in that the region coding for the polypeptide does not extend all the way through to the 5' terminus. This is a consequence of reverse transcriptase, an enzyme with inherently low "processivity" (a measure of the ability of the enzyme to remain attached to the template during the polymerisation reaction), failing to complete a DNA copy of the mRNA template during first strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., Proc Nat Acad Sci USA 85, 8998–9002, 1988). Recent modifications of the technique, exemplified by the Marathon (trade mark) technology (Clontech Laboratories Inc.) for example, have significantly simplified the search for longer cDNAs. In the Marathon (trade mark) technology, cDNAs have been prepared from mRNA extracted from a chosen tissue and an 'adaptor' sequence ligated onto each end. Nucleic acid amplification (PCR) is then carried out to amplify the "missing" 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate fill-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems comprising a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions there of for polynucleotides of the present invention. Polynucleotides may be introduced into host cells by methods described in many standard laboratory manuals, such as Davis et al, Basic Methods in Molecular Biology (1986) and Sambrook et al. (ibid). Preferred methods of introducing polynucleotides into host cells include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as Streptococci, Staphylococci, *E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector that is able to maintain, propagate or express a polynucleotide to produce a polypeptide in a host may be used. The appropriate polynucleotide sequence maybe inserted into an expression system by any of a variety of well-known and routine techniques, such as, for example, those set forth in Sambrook et al., (ibid). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during intracellular synthesis, isolation and/or purification.

Polynucleotides of the present invention may be used as diagnostic reagents, through detecting mutations in the associated gene. Detection of a mutated form of the gene characterized by the polynucleotide of SEQ ID NO:1 in the cDNA or genomic sequence and which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques well known in the art.

Nucleic acids for diagnosis may be obtained from a subject's cells, such as from blood, urine, saliva, tissue biopsy or autopsy material. The genomic DNA may be used directly for detection or it may be amplified enzymatically by using PCR, preferably RT-PCR, or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled rhotekin nucleotide sequences. Perfectly matched sequences can be distinguished from mismatched duplexes by RNase digestion or by differences in melting temperatures. DNA sequence difference may also be detected by alterations in the electrophoretic mobility of DNA fragments in gels, with or without denaturing agents, or by direct DNA sequencing (see, for instance, Myers et al., Science (1985) 230:1242). Sequence changes at specific locations may also be revealed by nuclease protection assays, such as RNase and S1 protection or the chemical cleavage method (see Cotton et al., Proc Natl Acad Sci USA (1985) 85: 4397–4401).

An array of oligonucleotides probes comprising rhotekin polynucleotide sequence or fragments thereof can be constructed to conduct efficient screening of e.g., genetic mutations. Such arrays are preferably high density arrays or grids. Array technology methods are well known and have general applicability and can be used to address a variety of questions in molecular genetics including gene expression, genetic linkage, and genetic variability, see, for example, M.Chee et al., Science, 274, 610–613 (1996) and other references cited therein.

Detection of abnormally decreased or increased levels of polypeptide or mRNA expression may also be used for diagnosing or determining susceptibility of a subject to a disease of the invention. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagonostic kit comprising:

(a) a polynucleotide of the present invention, preferably the nucleotide sequence of SEQ ID NO:1, or a fragment or an RNA transcript thereof;

(b) a nucleotide sequence complementary to that of (a);

(c) a polypeptide of the present invention, preferably the polypeptide of SEQ ID NO:2 or a fragment thereof or (d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease or susceptibility to a disease, particularly diseases of the invention, amongst others.

The polynucleotide sequences of the present invention are valuable for chromosome localisation studies. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (co-inheritance of physically adjacent genes). Precise human chromosomal localisations for a genomic sequence (gene fragment etc.) can be determined using Radiation Hybrid (RH) Mapping (Walter, M. Spillett, D., Thomas, P., Weissenbach, J., and Goodfellow, P., (1994) A method for constructing radiation hybrid maps of whole genomes, Nature Genetics 7, 22–28). A number of RH panels are available from Research Genetics (Huntsville, Ala., USA) e.g. the GeneBridge4 RH panel (Hum Mol Genet 1996 Mar;5(3):339–46 A radiation hybrid map of the human genome. Gyapay G, Schmitt K, Fizames C, Jones H, Vega-Czarny N, Spillett D, Muselet D, Prud'Homme J F, Dib C, Auffray C, Morissette J, Weissenbach J, Goodfellow P N). To determine the chromosomal location of a gene using this panel, 93 PCRs are performed using primers designed from the gene of interest on RH DNAs. Each of these DNAs contains random human genomic fragments maintained in a hamster background (human/hamster hybrid cell lines). These PCRs result in 93 scores indicating the presence or absence of the PCR product of the gene of interest. These scores are compared with scores created using PCR products from genomic sequences of known location. This comparison is conducted at http://www.genome.wi.mit.edu/. The gene of the present invention maps to human chromosome 2p13 between the markers D2S286 and D2S145.

The polynucleotide sequences of the present invention are also valuable tools for tissue expression studies. Such studies allow the determination of expression patterns of polynucleotides of the present invention which may give an indication as to the expression patterns of the encoded polypeptides in tissues, by detecting the mRNAs that encode them. The techniques used are well known in the art and include in situ hybridization techniques to clones arrayed on a grid, such as cDNA microarray hybridization (Schena et al, Science, 270, 467–470, 1995 and Shalon et al, Genome Res, 6, 639–645, 1996) and nucleotide amplification techniques such as PCR. A preferred method uses the TAQMAN (Trade mark) technology available from Perkin Elmer. Results from these studies can provide an indication of the normal function of the polypeptide in the organism. In addition, comparative studies of the normal expression pattern of mRNAs with that of mRNAs encoded by an alternative form of the same gene (for example, one having an alteration in polypeptide coding potential or a regulatory mutation) can provide valuable insights into the role of the polypeptides of the present invention, or that of inappropriate expression thereof in disease. Such inappropriate expression may be of a temporal, spatial or simply quantitative nature.

A further aspect of the present invention relates to antibodies. The polypeptides of the invention or their fragments, or cells expressing them, can be used as immunogens to produce antibodies that are immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole et al., Monoclonal Antibodies and Cancer Therapy, 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purity the polypeptides by affinity chromatography. Antibodies against polypeptides of the present invention may also be employed to treat diseases of the invention, amongst others.

Polypeptides and polynucleotides of the present invention may also be used as vaccines. Accordingly, in a further aspect, the present invention relates to a method for inducing an immunological response in a mammal that comprises inoculating the mammal with a polypeptide of the present invention, adequate to produce antibody and/or T cell immune response, including, for example, cytokine-producing T cells or cytotoxic T cells, to protect said animal from disease, whether that disease is already established within the individual or not. An immunological response in a mammal may also be induced by a method comprises delivering a polypeptide of the present invention via a vector directing expression of the polynucleotide and coding for the polypeptide in vivo in order to induce such an immunological response to produce antibody to protect said animal from diseases of the invention. One way of administering the vector is by accelerating it into the desired cells as a coating on particles or otherwise. Such nucleic acid vector may comprise DNA, RNA, a modified nucleic acid, or a DNA/RNA hybrid. For use a vaccine, a polypeptide or a nucleic acid vector will be normally provided as a vaccine formulation (composition). The formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions that may contain anti-oxidants, buffers, bacteriostats and solutes that render the formulation isotonic with the blood of the recipient; and aqueous and non-aqueous sterile suspensions that may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention have one or more biological functions that are of relevance in one or more disease states, in particular the diseases of the invention hereinbefore mentioned. It is therefore useful to identify compounds that stimulate or inhibit the function or level of the polypeptide. Accordingly, in a further aspect, the present invention provides for a method of screening compounds to identify those that stimulate or inhibit the function or level of the polypeptide. Such methods identify agonists or antagonists that may be employed for therapeutic and prophylactic purposes for such diseases of the invention as hereinbefore mentioned. Compounds may be identified from a variety of sources, for example, cells, cell-free preparations, chemical libraries, collections of chemical compounds, and natural product mixtures. Such agonists or antagonists so-identified may be natural or modified substrates, ligands, receptors, enzymes, etc., as the case may be, of the polypeptide; a structural or functional mimetic thereof (see Coligan et al., Current Protocols in Immunology 1(2):Chapter 5 (1991)) or a small molecule.

The screening method may simply measure the binding of a candidate compound to the polypeptide, or to cells or membranes bearing the polypeptide, or a fusion protein thereof, by means of a label directly or indirectly associated with the candidate compound. Alternatively, the screening method may involve measuring or detecting (qualitatively or quantitatively) the competitive binding of a candidate compound to the polypeptide against a labeled competitor (e.g.

agonist or antagonist). Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Further, the screening methods may simply comprise the steps of mixing a candidate compound with a solution containing a polypeptide of the present invention, to form a mixture, measuring a rhotekin activity in the mixture, and comparing the rhotekin activity of the mixture to a control mixture which contains no candidate compound.

Polypeptides of the present invention may be employed in conventional low capacity screening methods and also in high-throughput screening (HTS) formats. Such HTS formats include not only the well-established use of 96- and, more recently, 384-well microtiter plates but also emerging methods such as the nanowell method described by Schullek et al, Anal Biochem., 246, 20–29, (1997).

Fusion proteins, such as those made from Fc portion and rhotekin polypeptide, as hereinbefore described, can also be used for high-throughput screening assays to identify antagonists for the polypeptide of the present invention (see D. Bennett et al., J Mol Recognition, 8:52–58 (1995); and K. Johanson et al., J Biol Chem, 270(16):9459–9471 (1995)).

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents that may inhibit or enhance the production of polypeptide (also called antagonist or agonist, respectively) from suitably manipulated cells or tissues.

A polypeptide of the present invention may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide that compete with the binding of the polypeptide to its receptors, if any. Standard methods for conducting such assays are well understood in the art.

Examples of antagonists of polypeptides of the present invention include antibodies or, in some cases, oligonucleotides or proteins that are closely related to the ligands, substrates, receptors, enzymes, etc., as the case may be, of the polypeptide, e.g., a fragment of the ligands, substrates, receptors, enzymes, etc.; or a small molecule that bind to the polypeptide of the present invention but do not elicit a response, so that the activity of the polypeptide is prevented.

Screening methods may also involve the use of transgenic technology and rhotekin gene. The art of constructing transgenic animals is well established. For example, the rhotekin gene may be introduced through microinjection into the male pronucleus of fertilized oocytes, retroviral transfer into pre- or post-implantation embryos, or injection of genetically modified, such as by electroporation, embryonic stem cells into host blastocysts. Particularly useful transgenic animals are so-called "knock-in" animals in which an animal gene is replaced by the human equivalent within the genome of that animal. Knock-in transgenic animals are useful in the drug discovery process, for target validation, where the compound is specific for the human target. Other useful transgenic animals are so-called "knock-out" animals in which the expression of the animal ortholog of a polypeptide of the present invention and encoded by an endogenous DNA sequence in a cell is partially or completely annulled. The gene knock-out may be targeted to specific cells or tissues, may occur only in certain cells or tissues as a consequence of the limitations of the technology, or may occur in all, or substantially all, cells in the animal. Transgenic animal technology also offers a whole animal expression-cloning system in which introduced genes are expressed to give large amounts of polypeptides of the present invention.

Screening kits for use in the above described methods form a further aspect of the present invention. Such screening kits comprise:

(a) a polypeptide of the present invention;

(b) a recombinant cell expressing a polypeptide of the present invention;

(c) a cell membrane expressing a polypeptide of the present invention; or (d) an antibody to a polypeptide of the present invention; which polypeptide is preferably that of SEQ ID NO:2.

It will be appreciated that in any such kit, (a), (b), (c) or (d) may comprise a substantial component.

Glossary

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide" generally refers to any polyribonucleotide (RNA) or polydeoxribonucleotide (DNA), which may be unmodified or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any polypeptide comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques that are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, Proteins—Structure and Molecular Properties, 2nd Ed., T. E. Creighton, W. H. Freeman and Company, New York, 1993; Wold, F., Post-translational Protein Modifications: Perspectives and Prospects, 1–12, in Post-translational Covalent Modification of Proteins, B. C. Johnson, Ed., Academic Press, New York 1983; Seifter et al., "Analysis for protein modifications and nonprotein cofactors", Meth Enzymol, 182, 626–646, 1990, and Rattan et al., "Protein Synthesis: Post-translational Modifications and Aging", Ann NY Acad Sci, 663, 48–62, 1992).

"Fragment" of a polypeptide sequence refers to a polypeptide sequence that is shorter than the reference sequence but that retains essentially the same biological function or activity as the reference polypeptide. "Fragment" of a polynucleotide sequence refers to a polynucleotide sequence that is shorter than the reference sequence of SEQ ID NO:1.

"Variant" refers to a polynucleotide or polypeptide that differs from a reference polynucleotide or polypeptide, but retains the essential properties thereof. A typical variant of a polynucleotide differs in nucleotide sequence from the reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from the reference polypeptide. Generally, alterations are limited so that the sequences of the reference polypeptide and the variant are closely similar overall and, in many regions, identical. A variant and reference polypeptide may differ in amino acid sequence by one or more substitutions, insertions, deletions in any combination. A substituted or inserted amino acid residue may or may not be one encoded by the genetic code. Typical conservative substitutions include Gly, Ala; Val, Ile, Leu; Asp, Glu; Asn, Gln; Ser Thr; Lys, Arg; and Phe and Tyr. A variant of a polynucleotide or polypeptide may be naturally occurring such as an allele, or it may be a variant that is not known to occur naturally. Non-naturally occurring variants of polynucleotides and polypeptides may be made by mutagenesis techniques or by direct synthesis. Also included as variants are polypeptides having one or more post-translational modifications, for instance glycosylation, phosphorylation, methylation, ADP ribosylation and the like. Embodiments include methylation of the N-terminal amino acid, phosphorylations of serines and threonines and modification of C-terminal glycines.

"Allele" refers to one of two or more alternative forms of a gene occurring at a given locus in the genome.

"Polymorphism" refers to a variation in nucleotide sequence (and encoded polypeptide sequence, if relevant) at a given position in the genome within a population.

"Single Nucleotide Polymorphism" (SNP) refers to the occurrence of nucleotide variability at a single nucleotide position in the genome, within a population. An SNP may occur within a gene or within intergenic regions of the genome. Single Nucleotide Polymorphisms (SNPs) can be assayed using Allele Specific Amplification (ASA). For the process at least 3 primers are required. A common primer is used in reverse complement to the polymorphism being assayed. This common primer can be between 50 and 1500 bps from the polymorphic base. The other two (or more) primers are identical to each other except that the final 3' base wobbles to match one of the two (or more) alleles that make up the polymorphism. Two (or more) PCR reactions are then conducted on sample DNA, each using the common primer and one of the Allele Specific Primers.

"Splice Variant" as used herein refers to cDNA molecules produced from RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule each of that may encode different amino acid sequences. The term splice variant also refers to the proteins encoded by the above cDNA molecules.

"Identity" reflects a relationship between two or more polypeptide sequences or two or more polynucleotide sequences, determined by comparing the sequences. In general, identity refers to an exact nucleotide to nucleotide or amino acid to amino acid correspondence of the two polynucleotide or two polypeptide sequences, respectively, over the length of the sequences being compared.

"% Identity"—For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

"Similarity" is a further, more sophisticated measure of the relationship between two polypeptide sequences. In general, "similarity" means a comparison between the amino acids of two polypeptide chains, on a residue by residue basis, taking into account not only exact correspondences between a between pairs of residues, one from each of the sequences being compared (as for identity) but also, where there is not an exact correspondence, whether, on an evolutionary basis, one residue is a likely substitute for the other. This likelihood has an associated "score" from which the "% similarity" of the two sequences can then be determined.

Methods for comparing the identity and similarity of two or more sequences are well known in the art. Thus for instance, programs available in the Wisconsin Sequence Analysis Package, version 9.1 (Devereux J et al, Nucleic Acids Res, 12, 387–395, 1984, available from Genetics Computer Group, Madison, Wis., USA), for example the programs BESTFIT and GAP, may be used to determine the % identity between two polynucleotides and the % identity and the % similarity between two polypeptide sequences. BESTFIT uses the "local homology" algorithm of Smith and Waterman (J Mol Biol, 147,195–197, 1981, Advances in Applied Mathematics, 2, 482–489, 1981) and finds the best single region of similarity between two sequences. BEST-FIT is more suited to comparing two polynucleotide or two polypeptide sequences that are dissimilar in length, the program assuming that the shorter sequence represents a portion of the longer. In comparison, GAP aligns two sequences, finding a "maximum similarity", according to the algorithm of Neddleman and Wunsch (J Mol Biol, 48, 443–453, 1970). GAP is more suited to comparing sequences that are approximately the same length and an alignment is expected over the entire length. Preferably, the parameters "Gap Weight" and "Length Weight" used in each program are 50 and 3, for polynucleotide sequences and 12 and 4 for polypeptide sequences, respectively. Preferably, % identities and similarities are determined when the two sequences being compared are optimally aligned.

Other programs for determining identity and/or similarity between sequences are also known in the art, for instance the BLAST family of programs (Altschul S F et al, J Mol Biol, 215, 403–410, 1990, Altschul S F et al, Nucleic Acids Res., 25:389–3402, 1997, available from the National Center for Biotechnology Information (NCBI), Bethesda, Md., USA and accessible through the home page of the NCBI at www.ncbi.nlm.nih.gov) and FASTA (Pearson W R, Methods in Enzymology, 183, 63–99, 1990; Pearson W R and Lipman D J, Proc Nat Acad Sci USA, 85, 2444–2448,1988, available as part of the Wisconsin Sequence Analysis Package).

Preferably, the BLOSUM62 amino acid substitution matrix (Henikoff S and Henikoff J G, Proc. Nat. Acad Sci. USA, 89, 10915–10919, 1992) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a reference polynucleotide or a polypeptide sequence, the query and the reference sequence being optimally aligned and the parameters of the program set at the default value, as hereinbefore described.

"Identity Index" is a measure of sequence relatedness which may be used to compare a candidate sequence (polynucleotide or polypeptide) and a reference sequence. Thus, for instance, a candidate polynucleotide sequence having, for example, an Identity Index of 0.95 compared to a reference polynucleotide sequence is identical to the reference sequence except that the candidate polynucleotide sequence may include on average up to five differences per each 100 nucleotides of the reference sequence. Such differences are selected from the group consisting of at least one nucleotide deletion, substitution, including transition and transversion, or insertion. These differences may occur at the 5' or 3' terminal positions of the reference polynucleotide sequence or anywhere between these terminal positions, interspersed either individually among the nucleotides in the reference sequence or in one or more contiguous groups within the reference sequence. In other words, to obtain a polynucleotide sequence having an Identity Index of 0.95 compared to a reference polynucleotide sequence, an average of up to 5 in every 100 of the nucleotides of the in the reference sequence may be deleted, substituted or inserted, or any combination thereof as hereinbefore described. The same applies mutatis mutandis for other values of the Identity Index, for instance 0.96, 0.97, 0.98 and 0.99.

Similarly, for a polypeptide, a candidate polypeptide sequence having, for example, an Identity Index of 0.95 compared to a reference polypeptide sequence is identical to the reference sequence except that the polypeptide sequence may include an average of up to five differences per each 100 amino acids of the reference sequence. Such differences are selected from the group consisting of at least one amino acid deletion, substitution, including conservative and non-conservative substitution, or insertion. Thee differences may occur at the amino- or carboxy-terminal positions of the reference polypeptide sequence or anywhere between these terminal positions, interspersed either individually among the amino acids in the reference sequence or in one or more contiguous groups within the reference sequence. In other words, to obtain a polypeptide sequence having an Identity Index of 0.95 compared to a reference polypeptide sequence, an average of up to 5 in every 100 of the amino acids in the reference sequence may be deleted, substituted or inserted, or any combination thereof, as hereinbefore described. The same applies mutatis mutandis for other values of the Identity Index, for instance 0.96, 0.97, 0.98 and 0.99.

The relationship between the number of nucleotide or amino acid differences and the Identity Index may be expressed in the following equation:

$$n_a \leq x_a - (x_a \cdot I),$$

in which:

$n_a$ is the number of nucleotide or amino acid differences, $x_a$ is the total number of nucleotides or amino acids in SEQ ID NO:1 or SEQ ID NO:2, respectively, I is the Identity Index, · is the symbol for the multiplication operator, and which any non-integer product of $x_a$ and I is rounded down to the nearest integer prior to subtracting it from $x_a$.

"Homolog" is a generic term used in the art to indicate a polynucleotide or polypeptide sequence possessing a high degree of sequence relatedness to a reference sequence.

Such relatedness may be quantified by determining the degree of identity and/or similarity between the two sequences as hereinbefore defined. Falling within this generic term are the terns "ortholog", and "paralog". "Ortholog" refers to a polynucleotide or polypeptide that is the functional equivalent of the polynucleotide or polypeptide in another species. "Paralog" refers to a polynucleotide or polypeptide that within the same species which is functionally similar.

"Fusion protein" refers to a protein encoded by two, often unrelated, fused genes or fragments thereof. In one example, EP-A-0 464 *** discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 0232 262]. On the other hand, for some uses it would be desirable to be able to delete the Fc part after the fusion protein has been expressed, detected and purified.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

SEQUENCE INFORMATION

SEQ ID NO:1
ATGTTCTCCCGAAACCACCGGAGCCGGGTCACCGTGGCCAGGGGCTCCGC

CCTGGAGATGGAGTTCAAACGCGGCCGCTTCCGACTCAGCCTCTTCAGCG

ACCTGCCCGAGGACACGGAGTTGCAGAGGAAGCTAGACCATGAGATCCGG

ATGAGGGAAGGGGCCTGTAAGCTGCTGGCAGCCTGCTCCCAGCGAGAGCA

GGCTCTGGAGGCCACCAAGAGCCTGCTAGTGTGCAACAGCCGCATCCTCA

GCTACATGGGCGAGCTGCAGCGGCGCAAGGAGGCGCAGGTGCTGGGGAAG

ACAAGCCGGCGGCCTTCTGACAGTGGCCCGCCCGCTGAGCGCTCCCCCTG

CCGCGGCCGGGTCTGCATCTCTGACCTCCGGATTCCACTCATGTGGAAGG

ACACAGAATATTTCAAGAACAAAGGTGACTTGCACCGCTGGGCTGTGTTC

CTGCTGCTGCAGCTGGGGAACACATCCAGGACACAGAGATGATCCTAGT

GGACAGGACCCTCACAGACATCTCCTTTCAGAGCAATGTGCTCTTCGCTG

AGGCGGGGCCAGACTTTGAACTGCGGTTAGAGCTGTATGGGCCTGTGTG

GAAGAAGAGGGGGCCCTGACTGGCGGCCCCAAGAGGCTTGCCACCAAACT

CAGCAGCTCCCTGGGCCGCTCCTCAGGGAGGCGTGTCCGGGCATCGCTGG

ACAGTGCTGGGGGTTCAGGGAGCAGTCCCATCTTGCTCCCCACCCCAGTT

GTTGGTGGTCCTCGTTACCACCTCTTGGCTCACACCACACTCACCCTGGC

AGCAGTGCAAGATGGATTCCGCACACATGACCTCACCCTTGCCAGTCATG

AGGAGAACCCTGCCTGGCTGCCCCTTTATGGTAGCGTGTGTTGCCGTCTG

GCAGCTCAGCCTCTCTGCATGACTCAGCCCACTGCAAGTGGTACCCTCAG

GGTGCAGCAAGCTGGGGAGATGCAGAACTGGGCACAAGTGCATGGAGTTC

-continued
TGAAAGGCACAAACCTCTTCTGTTACCGGCAACCTGAGGATGCAGACACT

GGGGAAGAGCCGCTGCTTACTATTGCTGTCAACAAGGAGACTCGAGTCCG

GGCAGGGGAGCTGGACCAGGCTCTAGGACGGCCCTTCACCCTAAGCATCA

GTAACCAGTATGGGGATGATGAGGTGACACACACCCTTCAGACAGAAAGT

CGGGAAGCACTGCAGAGCTGGATGGAGGCTCTGTGGCAGCTTTTCTTTGA

CATGAGCCAATGGAAGCAGTGCTGTGATGAAATCATGAAAATTGAAACTC

CTGCTCCCCGGAAACCACCCCAAGCACTGGCAAAGCAGGGGTCCTTGTAC

CATGAGATGGCTATTGAGCCGCTGGATGACATCGCAGCGGTGACAGACAT

CCTGACCCAGCGGGAGGGCGCAAGGCTGGAGACACCCCCACCCTGGCTGG

CAATGTTTACAGACCAGCCTGCCCTGCCTAACCCCTGCTCGCCTGCCTCA

GTGGCCCCAGCCCCAGACTGGACCCACCCCCTGCCCTGGGGGAGACCCCG

AACCTTTTCCCTGGATGCTGTCCCCCCAGACCACTCCCCTAGGGCTCGCT

CGGTTGCCCCCCTCCCACCTCAGCGATCCCCACGGACCAGAGGCCTCTGC

AGCAAAGGCCAACCTCGCACTTGGCTCCAGTCACCAGTG

SEQ ID NO:2
MFSRNHRSRVTVARGSALEMEFKRGRFRLSLFSDLPEDTELQRKLDHEIR

MREGACKLLAACSQREQALEATKSLLVCNSRILSYMGELQRRKEAQVLGK

TSRRPSDSGPPAERSPCRGRVCISDLRIPLMWKDTEYFKNKGDLHRWAVF

LLLQLGEHIQDTEMILVDRTLTDISFQSNVLFAEAGPDFELRLELYGACV

EEEGALTGGPKRLATKLSSSLGRSSGRRVRASLDSAGGSGSSPILLPTPV

VGGPRYHLLAHTTLTLAAVQDGFRTHDLTLASHEENPAWLPLYGSVCCRL

AAQPLCMTQPTASGTLRVQQAGEMQNWAQVHGVLKGTNLFCYRQPEDADT

GEEPLLTIAVNKETRVRAGELDQALGRPFTLSISNQYGDDEVTHTLQTES

REALQSWMEALWQLFFDMSQWKQCCDEIMKIETPAPRKPPQALAKQGSLY

HEMAIEPLDDIAAVTDILTQREGARLETPPPWLAMFTDQPALPNPCSPAS

VAPAPDWTHPLPWGRPRTFSLDAVPPDHSPRARSVAPLPPQRSPRTRGLC

SKGQPRTWLQSPV

SEQ ID NO:3
GAGGACACGGAGTTGCAGAGGAAGCTAGACCATGAGATCCGGATGAGGGA

AGGGGCCTGTAAGCTGCTGGCAGCCTGCTCCCAGCGAGAGCAGGCTCTGG

AGGCCACCAAGAGCCTGCTAGTGTGCAACAGCCGCATCCTCAGCTACATG

GGCGAGCTGCAGCGGCGCAAGGAGCCCAGGTGCTGGGGAAGACAAGCCG

GCGNCATTCTGACAGTGGCCCGCCCGCTGAGCGCTCCCCCTGCCGCGGCC

GGGTCTGCATCTCTGACCTCCGGATTCCACTCATGTGGAAGGACACAGAA

TATTTCAAGAACAAAGGTGACTTGCACCGCTGGGCTGTGTTCCTGCTGCT

GCAGCTGGGGAACACATCCAGGACACAGAGATGATCCTAGTGGACAGGA

CCCTCACAGACATCTCCTTTCAGAGCAATGTGCTCTTCGCTGAGGCGGGG

CCAGACTTTGAACTGCGGTTAGAGCTGTATGGGCCTGTGTGGAAGAAGA

GGGGGCCCTGACTGGCGGCCCCAAGAGGCTTGCCACCAAACTCAGCAGCT

CCCTGGGCCGCTCCTCAGGGAGGCGTGTCCGGGCATCGCTGGACAGTGCT

GGGGGTTCAGGGAGCAGTCCCATCTTGCTCCCCACCCCAGTTGTTGGTGG

TCCTCGTTACCACCTCTTGGCTCACACCACACTCACCCTGGCAGCAGTGC

AAGATGGATTCCTCACACATGACCTCACCCTTGCCAGTCATGAGGAGAAC

CCTGCCTGGCTGCCCCTTTATGGTAGCGTGTGTTGCCGTCTGGCAGCTCA

GCCTCTCTGCATGACTCAGCCCACTGCAAGTGGTACCCTCAGGGTGCAGC

AAGCTGGGGAGATGCAGAACTGGGCACAAGTGCATGGAGTTCTGAAAGGC

ACAAACCTCTTCTGTTACCGGCAACCTGAGGATGCAGACACTGGGGAAGA

GCCGCTGTTTACTATTGCTGTCAACAAGGAGACTCGAGTCCGGGCAGGGG

AGCTGGACCAGGCTCTAGGNCGGCCCTTCACCCTAAGCATCAGTAACCAG

TATGGGGATGATGAGGTGACACACACCCTTCAGACAGAAAGTCGGGAAGC

ACTTCAGGCTTGGATGGAGGCTTTGTGGCAGCTTTTCTTTGACATGAGCC

AATGGAAGCAGTGCTGTGATGAAATCATGAAAATTGAAACTCCTGCTCCC

CGGAAACCACCCCAAGCACTGGCAAAGCAGGGGTCCTTGTACCATGAGAT

GGCTATTGAGCCGCTGGATGACATCGCAGCGGTGACAGACATCCTGACCC

AGCGGGAGGGCGCAAGGCTGGAGACACCCCCACCCTGGCTGGCAATGTTT

ACAGACCAGCCTGCCCTGCCTAACCCCTGCTCGCCTGCCTCAGTGGCCCC

AGCCCCAGACTGGACCCACCCCCTGCCCTGGGGGAGACCCCGAACCTTTT

CCCTGGATGCTGTCCCCCCAGACCACTCCCCTAGGGCTCGCTCGGTTGCC

CCCCTCCCACCTCAGCGATCCCCACGGACCAGAGGCCTCTGCAGCAAAGG

CCAACCTCGCACTTGGCTCCAGTCACCAGTGTGAGAGAGAAAGGTGCTGG

CATAGGATCTGCCCAGAAGAGAAAATGACCCATGCGCAGTTGGGCTCTGG

ATACGGCGCTGTCTATAGCAAGTTGGCCAGTCTGGCCTCCTGTTCCTCTG

CTGGACCTGGGGTAGGCTGCAGGGGTGGGCAGAAGCCCCTCTTAAATTGT

GGTTGCCATGGTACCGAGGGACTCATTCCTGGGGCTCGCTGGGACCTCCC

TAAACCCTTCCTGGAAGAAAACTGGAACCAACTCTGCCCTACCTCCCTGC

ACTAACCAGCTTTGAGGATGGCACTGAAGAACCCTTGGAGCAAACATACC

TCCCTTGTGACTCCCACATCAACCATTAAAGTTATTTAACAGCAGCCTTA

TTTATCTGGCTCCTGAGGAAAAA

SEQ ID NO:4

EDTELQRKLDHEIRMREGACKLLAACSQREQALEATKSLLVCNSRILSYM

GELQRRKEAQVLGKTSRRHSDSGPPAERSPCRGRVCISDLRIPLMWKDTE

YFKNKGDLHRWAVFLLLQLGEHIQDTEMILVDRTLTDISFQSNVLFAEAG

PDFELRLELYGACVEEEGALTGGPKRLATKLSSSLGRSSGRRVRASLDSA

GGSGSSPILLPTPVVGGPRYHLLAHTTLTLAAVQDGFLTHDLTLASHEEN

PAWLPLYGSVCCRLAAQPLCMTQPTASGTLRVQQAGEMQNWAQVHGVLKG

TNLFCYRQPEDADTGEEPLFTIAVNKETRVRAGELDQALGRPFTLSISNQ

YGDDEVTHTLQTESREALQAWMEALWQLFFDMSQWKQCCDEIMKIETPAP

RKPPQALAKQGSLYHEMAIEPLDDIAAVTDILTQREGARLETPPPWLAMF

TDQPALFNPCSPASVAPAPDWTHPLPWGRPRTFSLDAVPPDHSPRARSVA

PLPPQRSPRTRGLCSKGQPRTWLQSPV

---

What is claimed is:

1. A process for producing a polypeptide which comprises:

(a) culturing a host cell containing an exogenous vector wherein said vector contains in one contiguous sequence, an isolated polynucleotide encoding rhotekin of SEQ ID No:2, under conditions sufficient for the production of said polypeptide; and (b) recovering said polypeptide from the culture.

2. A process for producing a recombinant host cell which comprises the step of:

(a) introducing the exogenous expression vector of an isolated contiguous polynucleotide comprising a polynucleotide encoding a rhotekin having identity to the amino acid sequence set forth in SEQ ID No:2, and which has the rho binding function of rhotekin; and (b) selecting for the recombinant host cell that produces said rhotekin.

3. An isolated recombinant host cell containing an exogenous vector wherein said vector contains in one contiguous sequence, an isolated polynucleotide encoding rhotekin of SEQ ID No:2.

4. An isolated polynucleotide comprising a contiguous polynucleotide sequence encoding a rhotekin set forth in SEQ ID No:2, and which has the rho binding function of rhotekin.

5. An expression vector comprising a polynucleotide of claim 4 in operative linkage to control elements effecting expression.

6. The isolated polynucleotide of claim 4 consisting of the polynucleotide sequence set forth in SEQ ID No:1.

7. An isolated polynucleotide which is fully complementary to the isolated polynucleotide encoding the amino acid sequence set forth in SEQ ID No:2.

8. The isolated polynucleotide of claim 7 which is fully complementary to the polynucleotide sequence set forth in SEQ ID No:1.

* * * * *

SEQUENCE LISTING

<160> NUMBER OF SEQ ID NOS: 4

<210> SEQ ID NO 1
<211> LENGTH: 1689
<212> TYPE: DNA
<213> ORGANISM: Homo sapiens

<400> SEQUENCE: 1
atgttctccc gaaaccaccg gagccgggtc accgtggcca ggggctccgc cctggagatg      60
gagttcaaac gcggccgctt ccgactcagc ctcttcagcg acctgcccga ggacacggag     120
ttgcagagga agctagacca tgagatccgg atgagggaag gggcctgtaa gctgctggca     180
gcctgctccc agcgagagca ggctctggag gccaccaaga gcctgctagt gtgcaacagc     240
cgcatcctca gctacatggg cgagctgcag cggcgcaagg aggcgcaggt gctggggaag     300
acaagccggc ggccttctga cagtggcccg cccgctgagc gctcccctg ccgcggccgg     360 gtctgcatct ctgacctccg gattccactc atgtggaagg acacagaata tttcaagaac     420
aaaggtgact gcaccgctg gctgtgttc ctgctgctga gctgggggga acacatccag     480
gacacagaga tgatcctagt ggacaggacc ctcacagaca tctcctttca gagcaatgtg     540

```
ctcttcgctg aggcggggcc agactttgaa ctgcggttag agctgtatgg ggcctgtgtg    600
gaagaagagg gggccctgac tggcggcccc aagaggcttg ccaccaaact cagcagctcc    660
ctgggccgct cctcagggag cgtgtccgg gcatcgctgg acagtgctgg gggttcaggg     720
agcagtccca tcttgctccc cacccagtt gttggtggtc ctcgttacca cctcttggct     780
cacaccacac tcaccctggc agcagtgcaa gatggattcc gcacacatga cctcacccct    840
gccagtcatg aggagaaccc tgcctggctg ccccttttatg gtagcgtgtg ttgccgtctg   900
gcagctcagc ctctctgcat gactcagccc actgcaagtg gtaccctcag ggtgcagcaa    960
gctggggaga tgcagaactg ggcacaagtg catggagttc tgaaaggcac aaacctcttc    1020
tgttaccggc aacctgagga tgcagacact ggggaagagc cgctgcttac tattgctgtc    1080
aacaaggaga ctcgagtccg ggcaggggag ctggaccagg ctctaggacg gcccttcacc    1140
ctaagcatca gtaaccagta tgggatgat gaggtgacac acaccttca gacagaaagt     1200 cgggaagcac tgcagagctg gatggaggct ctgtggcagc ttttctttga catgagccaa    1260
tggaagcagt gctgtgatga aatcatgaaa attgaaactc ctgctccccg gaaaccaccc    1320
caagcactgg caaagcaggg gtccttgtac catgagatgg ctattgagcc gctggatgac    1380
atcgcagcgg tgacagacat cctgacccag cgggagggcg caaggctgga cacccccca    1440 ccctggctgg caatgtttac agaccagcct gccctgccta cccctgctc gcctgcctca    1500 gtggccccag cccagactg gacccacccc ctgccctggg ggagacccg aacctttttcc   1560 ctggatgctg tcccccaga ccactccct agggctcgct cggttgcccc cctcccacct     1620
cagcgatccc cacggaccag aggcctctgc agcaaaggcc aacctcgcac ttggctccag   1680
tcaccagtg                                                           1689
```

<210> SEQ ID NO 2
<211> LENGTH: 563
<212> TYPE: PRT
<213> ORGANISM: Homo sapiens

<400> SEQUENCE: 2

```
Met Phe Ser Arg Asn His Arg Ser Arg Val Thr Val Ala Arg Gly Ser
 1               5                  10                  15

Ala Leu Glu Met Glu Phe Lys Arg Gly Arg Phe Arg Leu Ser Leu Phe
            20                  25                  30

Ser Asp Leu Pro Glu Asp Thr Glu Leu Gln Arg Lys Leu Asp His Glu
        35                  40                  45

Ile Arg Met Arg Glu Gly Ala Cys Lys Leu Leu Ala Ala Cys Ser Gln
    50                  55                  60

Arg Glu Gln Ala Leu Glu Ala Thr Lys Ser Leu Leu Val Cys Asn Ser
65                  70                  75                  80

Arg Ile Leu Ser Tyr Met Gly Glu Leu Gln Arg Lys Glu Ala Gln
                85                  90                  95

Val Leu Gly Lys Thr Ser Arg Arg Pro Ser Asp Ser Gly Pro Pro Ala
           100                 105                 110

Glu Arg Ser Pro Cys Arg Gly Arg Val Cys Ile Ser Asp Leu Arg Ile
        115                 120                 125

Pro Leu Met Trp Lys Asp Thr Glu Tyr Phe Lys Asn Lys Gly Asp Leu
    130                 135                 140

His Arg Trp Ala Val Phe Leu Leu Gln Leu Gly Glu His Ile Gln
145                 150                 155                 160

Asp Thr Glu Met Ile Leu Val Asp Arg Thr Leu Thr Asp Ile Ser Phe
```

```
                165                 170                 175
Gln Ser Asn Val Leu Phe Ala Glu Ala Gly Pro Asp Phe Glu Leu Arg
            180                 185                 190
Leu Glu Leu Tyr Gly Ala Cys Val Glu Glu Gly Ala Leu Thr Gly
        195                 200                 205
Gly Pro Lys Arg Leu Ala Thr Lys Leu Ser Ser Leu Gly Arg Ser
    210                 215                 220
Ser Gly Arg Arg Val Arg Ala Ser Leu Asp Ser Ala Gly Gly Ser Gly
225                 230                 235                 240
Ser Ser Pro Ile Leu Leu Pro Thr Pro Val Gly Gly Pro Arg Tyr
                245                 250                 255
His Leu Leu Ala His Thr Thr Leu Thr Leu Ala Ala Val Gln Asp Gly
            260                 265                 270
Phe Arg Thr His Asp Leu Thr Leu Ala Ser His Glu Glu Asn Pro Ala
        275                 280                 285
Trp Leu Pro Leu Tyr Gly Ser Val Cys Cys Arg Leu Ala Ala Gln Pro
    290                 295                 300
Leu Cys Met Thr Gln Pro Thr Ala Ser Gly Thr Leu Arg Val Gln Gln
305                 310                 315                 320
Ala Gly Glu Met Gln Asn Trp Ala Gln Val His Gly Val Leu Lys Gly
                325                 330                 335
Thr Asn Leu Phe Cys Tyr Arg Gln Pro Glu Asp Ala Asp Thr Gly Glu
            340                 345                 350
Glu Pro Leu Leu Thr Ile Ala Val Asn Lys Glu Thr Arg Val Arg Ala
        355                 360                 365
Gly Glu Leu Asp Gln Ala Leu Gly Arg Pro Phe Thr Leu Ser Ile Ser
    370                 375                 380
Asn Gln Tyr Gly Asp Asp Glu Val Thr His Thr Leu Gln Thr Glu Ser
385                 390                 395                 400
Arg Glu Ala Leu Gln Ser Trp Met Glu Ala Leu Trp Gln Leu Phe Phe
                405                 410                 415
Asp Met Ser Gln Trp Lys Gln Cys Cys Asp Glu Ile Met Lys Ile Glu
            420                 425                 430
Thr Pro Ala Pro Arg Lys Pro Pro Gln Ala Leu Ala Lys Gln Gly Ser
        435                 440                 445
Leu Tyr His Glu Met Ala Ile Glu Pro Leu Asp Asp Ile Ala Ala Val
    450                 455                 460
Thr Asp Ile Leu Thr Gln Arg Glu Gly Ala Arg Leu Glu Thr Pro Pro
465                 470                 475                 480
Pro Trp Leu Ala Met Phe Thr Asp Gln Pro Ala Leu Pro Asn Pro Cys
                485                 490                 495
Ser Pro Ala Ser Val Ala Pro Ala Asp Trp Thr His Pro Leu Pro
            500                 505                 510
Trp Gly Arg Pro Arg Thr Phe Ser Leu Asp Ala Val Pro Pro Asp His
        515                 520                 525
Ser Pro Arg Ala Arg Ser Val Ala Pro Leu Pro Gln Arg Ser Pro
    530                 535                 540
Arg Thr Arg Gly Leu Cys Ser Lys Gly Gln Pro Arg Thr Trp Leu Gln
545                 550                 555                 560
Ser Pro Val

<210> SEQ ID NO 3
<211> LENGTH: 1973
```

<212> TYPE: DNA
<213> ORGANISM: Homo sapiens
<220> FEATURE:
<221> NAME/KEY: unsure
<222> LOCATION: (204)(1020)

<400> SEQUENCE: 3

```
gaggacacgg agttgcagag gaagctagac catgagatcc ggatgaggga agggggcctgt    60
aagctgctgg cagcctgctc ccagcgagag caggctctgg aggccaccaa gagcctgcta   120
gtgtgcaaca gccgcatcct cagctacatg ggcgagctgc agcggcgcaa ggaggcccag   180
gtgctgggga agacaagccg gcgncattct gacagtggcc cgcccgctga gcgctccccc   240
tgccgcggcc gggtctgcat ctctgacctc cggattccac tcatgtggaa ggacacagaa   300
tatttcaaga acaaaggtga cttgcaccgc tgggctgtgt tcctgctgct gcagctgggg   360
gaacacatcc aggacacaga gatgatccta gtggacagga ccctcacaga catctccttt   420
cagagcaatg tgctcttcgc tgaggcgggg ccagactttg aactgcggtt agagctgtat   480
ggggcctgtg tggaagaaga gggggccctg actggcggcc caagaggct tgccaccaaa    540
ctcagcagct ccctgggccg ctcctcaggg aggcgtgtcc gggcatcgct ggacagtgct   600
gggggttcag ggagcagtcc catcttgctc cccaccccag ttgttggtgg tcctcgttac   660
cacctcttgg ctcacaccac actcaccctg gcagcagtgc aagatggatt cctcacacat   720
gacctcaccc ttgccagtca tgaggagaac cctgcctggc tgccccttta tggtagcgtg   780
tgttgccgtc tggcagctca gcctctctgc atgactcagc ccactgcaag tggtaccctc   840
agggtgcagc aagctgggga gatgcagaac tgggcacaag tgcatggagt tctgaaaggc   900
acaaacctct tctgttaccg gcaacctgag gatgcagaca ctgggggaaga gccgctgttt   960
actattgctg tcaacaagga gactcgagtc cgggcagggg agctggacca ggctctaggn  1020
cggcccttca ccctaagcat cagtaaccag tatgggggatg atgaggtgac acacaccctt  1080
cagacagaaa gtcgggaagc acttcaggct tggatggagg ctttgtggca gcttttcttt  1140
gacatgagcc aatggaagca gtgctgtgat gaaatcatga aaattgaaac tcctgctccc  1200
cggaaaccac cccaagcact ggcaaagcag gggtccttgt accatgagat ggctattgag  1260
ccgctggatg acatcgcagc ggtgacagac atcctgaccc agcgggaggg cgcaaggctg  1320
gagacacccc caccctggct ggcaatgttt acagaccagc ctgccctgcc taaccccctgc  1380
tcgcctgcct cagtggcccc agccccagac tggacccacc cctgccctg gggagaccc    1440
cgaaccttt cctggatgc tgtccccca gaccactccc ctagggctcg ctcggttgcc     1500
cccctcccac ctcagcgatc cccacggacc agaggcctct gcagcaaagg ccaacctcgc  1560
acttggctcc agtcaccagt gtgagagaga aaggtgctgg cataggatct gcccagaaga  1620
gaaaatgacc catgcgcagt tgggctctgg atacggcgct gtctatagca agttggccag  1680
tctggcctcc tgttcctctg ctggacctgg ggtaggctgc aggggtgggc agaagcccct  1740
cttaaattgt ggttgccatg gtaccgaggg actcattcct ggggctcgct gggacctccc  1800
taaaccttc ctggaagaaa actggaacca actctgccct acctccctgc actaaccagc   1860
tttgaggatg gcactgaaga acccttggag caaacatacc tcccttgtga ctcccacatc  1920
aaccattaaa gttatttaac agcagcctta tttatctggc tcctgaggaa aaa         1973
```

<210> SEQ ID NO 4
<211> LENGTH: 527
<212> TYPE: PRT
<213> ORGANISM: Homo sapiens

<400> SEQUENCE: 4

```
Glu Asp Thr Glu Leu Gln Arg Lys Leu Asp His Glu Ile Arg Met Arg
 1               5                  10                  15
Glu Gly Ala Cys Lys Leu Leu Ala Ala Cys Ser Gln Arg Glu Gln Ala
            20                  25                  30
Leu Glu Ala Thr Lys Ser Leu Leu Val Cys Asn Ser Arg Ile Leu Ser
        35                  40                  45
Tyr Met Gly Glu Leu Gln Arg Arg Lys Glu Ala Gln Val Leu Gly Lys
50                  55                  60
Thr Ser Arg Arg His Ser Asp Ser Gly Pro Pro Ala Glu Arg Ser Pro
65                  70                  75                  80
Cys Arg Gly Arg Val Cys Ile Ser Asp Leu Arg Ile Pro Leu Met Trp
                85                  90                  95
Lys Asp Thr Glu Tyr Phe Lys Asn Lys Gly Asp Leu His Arg Trp Ala
            100                 105                 110
Val Phe Leu Leu Gln Leu Gly Glu His Ile Gln Asp Thr Glu Met
        115                 120                 125
Ile Leu Val Asp Arg Thr Leu Thr Asp Ile Ser Phe Gln Ser Asn Val
130                 135                 140
Leu Phe Ala Glu Ala Gly Pro Asp Phe Glu Leu Arg Leu Glu Leu Tyr
145                 150                 155                 160
Gly Ala Cys Val Glu Glu Gly Ala Leu Thr Gly Pro Lys Arg
                165                 170                 175
Leu Ala Thr Lys Leu Ser Ser Ser Leu Gly Arg Ser Gly Arg Arg
            180                 185                 190
Val Arg Ala Ser Leu Asp Ser Ala Gly Gly Ser Gly Ser Ser Pro Ile
        195                 200                 205
Leu Leu Pro Thr Pro Val Val Gly Gly Pro Arg Tyr His Leu Leu Ala
        210                 215                 220
His Thr Thr Leu Thr Leu Ala Ala Val Gln Asp Gly Phe Leu Thr His
225                 230                 235                 240
Asp Leu Thr Leu Ala Ser His Glu Glu Asn Pro Ala Trp Leu Pro Leu
                245                 250                 255
Tyr Gly Ser Val Cys Cys Arg Leu Ala Ala Gln Pro Leu Cys Met Thr
            260                 265                 270
Gln Pro Thr Ala Ser Gly Thr Leu Arg Val Gln Gln Ala Gly Glu Met
        275                 280                 285
Gln Asn Trp Ala Gln Val His Gly Val Leu Lys Gly Thr Asn Leu Phe
290                 295                 300
Cys Tyr Arg Gln Pro Glu Asp Ala Asp Thr Gly Glu Pro Leu Phe
305                 310                 315                 320
Thr Ile Ala Val Asn Lys Glu Thr Arg Val Arg Ala Gly Glu Leu Asp
                325                 330                 335
Gln Ala Leu Gly Arg Pro Phe Thr Leu Ser Ile Ser Asn Gln Tyr Gly
            340                 345                 350
Asp Asp Glu Val Thr His Thr Leu Gln Thr Glu Ser Arg Glu Ala Leu
        355                 360                 365
Gln Ala Trp Met Glu Ala Leu Trp Gln Leu Phe Phe Asp Met Ser Gln
        370                 375                 380
Trp Lys Gln Cys Cys Asp Glu Ile Met Lys Ile Glu Thr Pro Ala Pro
385                 390                 395                 400
Arg Lys Pro Pro Gln Ala Leu Ala Lys Gln Gly Ser Leu Tyr His Glu
```

-continued

```
                405                 410                 415

Met Ala Ile Glu Pro Leu Asp Asp Ile Ala Ala Val Thr Asp Ile Leu
            420                 425                 430

Thr Gln Arg Glu Gly Ala Arg Leu Glu Thr Pro Pro Pro Trp Leu Ala
        435                 440                 445

Met Phe Thr Asp Gln Pro Ala Leu Pro Asn Pro Cys Ser Pro Ala Ser
    450                 455                 460

Val Ala Pro Ala Pro Asp Trp Thr His Pro Leu Pro Trp Gly Arg Pro
465                 470                 475                 480

Arg Thr Phe Ser Leu Asp Ala Val Pro Pro Asp His Ser Pro Arg Ala
            485                 490                 495

Arg Ser Val Ala Pro Leu Pro Pro Gln Arg Ser Pro Arg Thr Arg Gly
            500                 505                 510

Leu Cys Ser Lys Gly Gln Pro Arg Thr Trp Leu Gln Ser Pro Val
        515                 520                 525
```